United States Patent [19]

Hemmilä et al.

[11] Patent Number: 4,565,790
[45] Date of Patent: Jan. 21, 1986

[54] METHOD FOR FLUORESCENCE SPECTROSCOPIC DETERMINATION OF A BIOLOGICALLY ACTIVE SUBSTANCE

[75] Inventors: Ilkka Hemmilä, Turku, Finland; Salifu Dakubu, London, England

[73] Assignee: WALLAC Oy, Turku, Finland

[21] Appl. No.: 513,744

[22] Filed: Jul. 14, 1983

Related U.S. Application Data

[63] Continuation-in-part of Ser. No. 368,274, Apr. 14, 1982, abandoned.

[30] Foreign Application Priority Data

Apr. 30, 1981 [SE] Sweden .............................. 8102753

[51] Int. Cl.$^4$ .................. G01N 33/536; G01N 33/533
[52] U.S. Cl. ..................................... 436/537; 436/546; 436/800; 436/805; 436/825
[58] Field of Search ............... 436/536, 537, 546, 800, 436/805, 825

[56] References Cited

U.S. PATENT DOCUMENTS 4,283,382  8/1981  Frank et al. .......................... 436/546
4,341,957  7/1982  Wieder ............................. 250/461.2

OTHER PUBLICATIONS

Wieder, Chem. Abs., vol. 90, 1979, 90:99557e, (citing Immounoflouresc. Tech. Proc. Int. Conf. 6th, 1978, p. 67080).
Makhijani et al., J. Ind. Chem. Soc., vol. 60, 1978, pp. 840 and 841.
Nakatani et al., Rev. Phys. Chem., Japan, vol. 42, 1972, pp. 103 to 107.
Moller et al., Chem. Rev., vol. 65, 1965, pp. 1, 10, 13 and 25 to 50.

*Primary Examiner*—Christine M. Nucker
*Attorney, Agent, or Firm*—Fisher, Christen & Sabol

[57] ABSTRACT

Method for fluorescence spectroscopic determination of a biological substance provided with a marker consisting of a lanthanide chelate complex formed by a lanthanide coupled to the substance via a chelate forming compound, such as an EDTA-analogue, the lanthanide ion before the detection is dissociated from the active substance for instance by adding a buffer with a pH value below 3.5 and a splitting detergent, whereafter the excitation in the determination takes place in the solution in the presence of a $\beta$-diketone by using a short radiation pulse and the fluorescence from the marker is detected when the fluorescence from the noise sources has substantially ceased.

10 Claims, 3 Drawing Figures

METHOD FOR FLUORESCENCE SPECTROSCOPIC DETERMINATION OF A BIOLOGICALLY ACTIVE SUBSTANCE

This is a continuation-in-part of application Ser. No. 368,274, filed on April 14, 1982, now abandoned.

BACKGROUND OF THE INVENTION

1. Field of the Invention

The present invention refers to a method for fluorescence spectroscopic determination of a biological substance provided with a marker consisting of a lanthanide chelate complex formed by a lanthanide coupled to the substance via a chelate forming compound, such as an EDTA-analogue.

2. Prior art

In quantitative immunological determinations an antibody or an antigen or its conjugate is usually provided with an easily detectable marker which at present usually consists of a radioactive isotope. The disadvantages of using radioactive isotopes are their limited storage time and the fact that one wishes to decrease the use of radioactive substances within medicine for health and environment reasons. An alternative to the radioimmunological methods are the fluoroimmunological methods where the marker is a fluorescent substance.

A special problem in fluorescence determinations within the immunological field is that serum has a relatively strong fluorescence which gives rise to high background levels for most fluorescence markers. This fluorescence of serum derives mainly from different proteins which however have relatively short excitation and emission wavelengths (excitation maximum at 280 nm, emission maximum at 340 nm) and thus it does not constitute a significant source of noise. Serum does however also give rise to other types of fluorescence, presumably deriving from other compounds than protein, this fluorescence appearing at longer wavelengths (excitation at 340 nm, emission at 460 to 470 nm) and thus gives rise to noise phenomena which are more difficult to deal with. In addition to the inherent fluorescence of serum the background is also affected by the scattering of the sample. The scattering gives rise to an interference, especially if markers with a small Stoke's shift (less than 50 nm) are used. Because of the high background fluorescence and the scattering of the fluorescence the sensitivity of markers is decreased by 50 to 100 times if used in serum as compared to their use in pure buffer.

Another problem arises in the fluorescence determination where the antibodies and the biologically active compound which is subject to the analysis are attached to a surface such as the wall of a test tube in addition to their internal coupling. Thus, the attached compounds have a strong inherent fluorescence and the surface made of glass or plastic is often also fluorescent and additionally has disturbing light scattering properties. The fluorescence measuring from a surface is thus more difficult from a measuring point of view than the measurement of a solution.

The requirements of a marker which is used in an immunological system are that it has to have as high a fluorescence as possible, a relatively long emission wavelength (more than 500 nm), a high Stoke's shift and the property of being coupled (covalently to the antibody or the antigen) without a negative effect on the conjugation properties.

A fluorescent marker meeting these requirements is described in the Swedish patent application No. 7902078-8 and is formed by a lanthanide chelate made up from a lanthanide and an aromatic β-diketone, which is coupled to the compound via an EDTA-analogue so as to obtain a fluorescent lanthanide complex. This marker furthermore has the essential property of a long fluorescent time, 50 to 1000 μsec which makes it possible to use an instrumentation technique described for instance in U.S. Pat. No. 4,058,732 in accordance with which the sample is excited by a laser pulse of a short duration, the fluorescence being detected only when the fluorescence from the noise sources has declined.

The disadvantage of using the above described marker is that the β-diketones disturb the immunoreaction and when they are supplied after the termination of the immumoreaction a very long time is required for the formation of the ternary chelate and furthermore, the protein used is often coupled to a surface, for instance, the wall of a test tube which makes measurements of a sufficient accuracy difficult to carry out.

BROAD DESCRIPTION OF THE INVENTION

It is an object of the present invention to provide a method in which these disadvantages are eliminated and according to which the measurement can be carried out after a very short time with a high accuracy.

This invention involves a method for fluorescence spectroscopic determination of a biological substance provided with a marker consisting of a lanthanide chelate complex formed of a lanthanide coupled to the substance via a chelate forming compound, such as, an EDTA-analogue. The lanthanide ion before the detection is split from the active substance. Thereafter the excitation in the determination takes place in the solution by using a short radiation pulse and the fluorescence from the marker is detected when the fluorescence from the noise sources has substantially ceased. The split can take place by adding a buffer with a pH-value below 3.5, containing a detergent, such as Triton X-100 (an alkyl aryl polyether alcohol), a β-diketone and a Lewis base, for example, trioctylphosphineoxide.

DETAILED DESCRIPTION OF THE INVENTION

According to the invention a lanthanide, for instance europium, is separated from EDTA at a low pH-value, suitably below 3.5, in a solution containing a suitable detergent, such as Triton X-100, and a β-diketone to amplify the fluorescence after the separation. The following table gives examples of some of the β-diketones well suited for this purpose:

| β-diketone $R_1$—CO—CH$_2$—CO—$R_2$ | $R_1$ | $R_2$ |
| --- | --- | --- |
| 2-naphthoyltrifluoroacetone (2-NTA) | 2-naphthyl | $CF_3$ |
| 1-naphthoyltrifluoroacetone (1-NTA) | 1-naphthyl | $CF_3$ |
| p-methoxybenzoyltrifluoroac. | p-methoxy- | $CF_3$ |

| | | |
|---|---|---|
| (MO-BTA) | phenyl | |
| p-fluorobenzoyltrifluoroac. (F-BTA) | p-fluorophenyl | CF$_3$ |
| benzoyltrifluoroacetone (BTA) | phenyl | CF$_3$ |
| furoyltrifluoroacetone (FTA) | 2-furyl | CF$_3$ |
| naphthoylfuroylmethane (NFM) | 2-naphthyl | 2-furyl |
| dithenoylmethane (DTM) | 2-thenyl | 2-thenyl |
| dibenzoylmethane (DBM) | phenyl | phenyl |

In order to further improve the fluorescence, especially in water solutions, since water has a strong inhibitory effect, some synergistic compound such as a so called Lewis base should be added. A group of such bases consists of N-heterocyclic compounds such as o-phenanthroline and another group consists of phosphines and phosphine oxides, e.g. trioctylphosphineoxide (TOPO). The properties of these compounds and the way in which they affect the fluorescence are described for instance in the following publications: Halverson, (1964), J. Chem. Phys. 41, 157; Kareseva and Karesev, (1975), Koord. Khim. 1, 926; Muraveva, (1977), Zh. Neorg. Khim. 22, 3009; Makarchuk, (1979), Ukr. Khim. Zh. 45, 656; Taketatsu, (1979), Anal. Chim. Acta 108, 429; and Brittain, (1980), Inorg. Chem. 19, 640.

According to the invention the measuring could take place for instance in a system consisting of a buffer with pH 2.8 to 3.5 (for instance phthalate-HCL) containing 2-NTA 10 to 100 $\mu$M, TOPO 10 to 100 $\mu$M and Triton X-100 0.1 to 0.5 percent.

Figure 1:
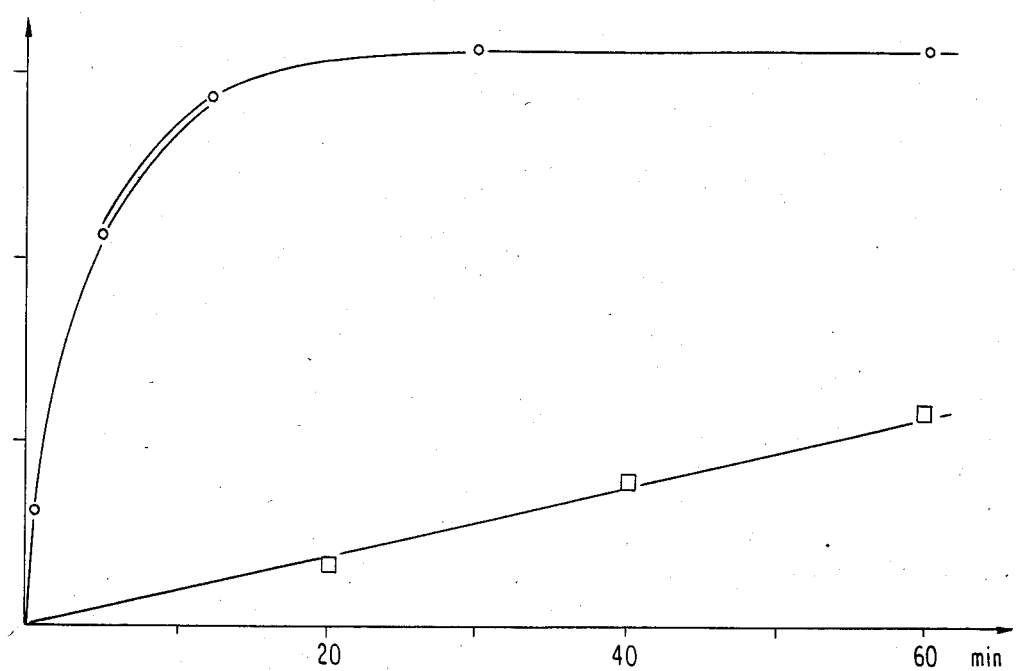
FIG. 1 is a fluorescence curve of invention system versus the prior system.

The diagram in FIG. 1 shows the fluorescence in such a system (curve marked by circles) developed as the function of time as compared to the systeem where the lanthanide is coupled to the protein (curve marked by squares).

The method according to the invention has been tested by using europium in a model system in which the europium was coupled to IgG of sheep-anti-rabbit IgG and the same protein as an antibody in a solid phase with rabbit IgG as antigen. Both methods give roughly the same standard curve. The essential advantage of the method according to the invention is that measurement can take place at an earlier time (after about 30 minutes of incubation as compared to 8 to 10 hours) and with a higher accuracy and a higher fluorescent intensity.

The invention is further illustrated by the following non-limiting examples:

EXAMPLE 1

Measurement of rabbit IgG (RIgG) in a time-resolved immunofluorometric assay

Labelling of sheep-anti-rabbit IgG: Conjugation of diazophenyl-EDTA-Eu to the antibody preparation was carried out by careful neutralization of an acidic stock solution of diazotized material to a pH of 5 to 6 with saturated sodium hydrogen carbonate and adding this reagent to the antibody solution in 5 to 100 molar excess. The conjugation was made overnight in a 0.2 M borate buffer at +4° C. The pH was kept between 8.5 and 9.5 by the addition of NaOH. The labelled antibody was purified from excess free conjugate on a 1.5×25 cm Sephadex G50 column by using 0.05 M Tris-Hcl buffer, pH 7.7, containing 9 g/l of NaCl and 0.05 percent of NaN$_3$ as the eluting agent. The conjugation ratio was calculated by measuring the Eu fluorescence and comparing it to known EuCl$_3$ standards.

Immunoassay: Non-covalent coating of polystyrene tubes was done in 0.2 M borate buffer pH 9.3 using 2 $\mu$g of sheep-anti-rabbit IgG/tube and incubating overnight at room temperature. After coating the tubes were washed and saturated with 0.5 percent BSA for 2 hr. and stored wet at +4° C.

The immunoreactions were carried out in 0.05 M Tris-HCl buffer, pH 7.7, containing 9 g/l of NaCl, 0.05 percent of NaN$_3$, 0.5 percent of BSA, 0.05 percent of bovine globulin and 20 $\mu$M of EDTA. The first incubation (1 hr, 30° C.) was carried out in the presence of various amounts of RIGG and the second (1 hr, 30° C.) in the presence of 50 ng of Eulabelled sheep-anti-rabbit IgG, after which the tubes were washed three times.

The europium was released and the fluorescence of the label was enhanced by the addition of 0.5 ml/tube of a solution with the following composition: 0.1 M acetate buffer adjusted to pH 3.2 with potassium hydrogen, phthalate, containing 15 $\mu$M of 2-NTA, 50 $\mu$M of TOPO and 0.1 percent Triton X-100. The fluorescence was measured 20 minutes after the addition by means of a single photon counting time-resolved fluorometer using a xenon flash lamp (1000 Hz) for a total measuring time of 1 sec., with a 50 $\mu$sec delay time and a 250 $\mu$sec counting time.

Figure 2:
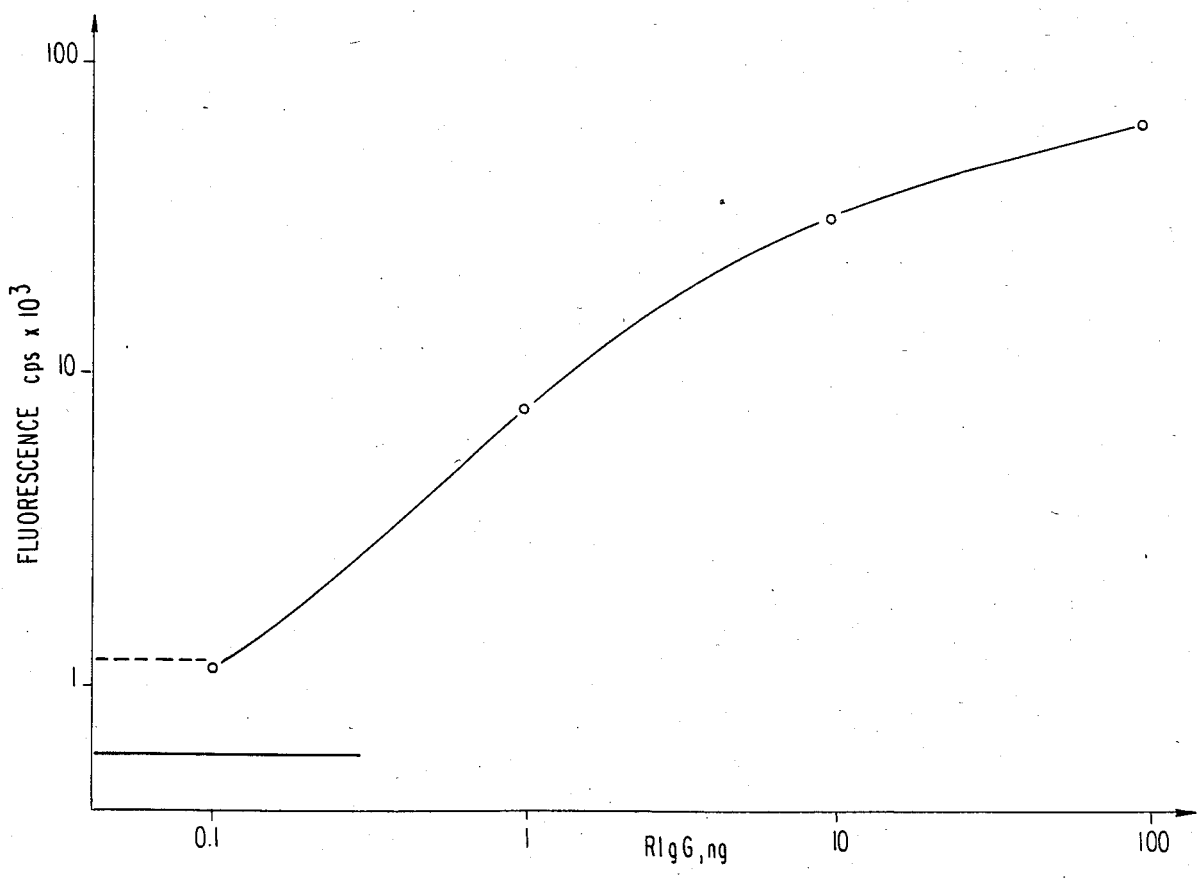
FIG. 2 is a graph of a standard assay curve for RIgG re Example 1.

The result of a typical assay, a standard curve for RIgG, is presented in FIG. 2.

EXAMPLE 2

A time-resolved fluoroimmunoassay of HBsAg

Labelling of antibody: The labelled antibody was prepared by conjugating a diazotized aminophenyl-EDTA-Eu complex to affinity purified HBsAg antibodies from ascites fluid according to the same procedure as described in Example 1.

Immunoassay: The coating with the antibody was performed in 0.2 M borate buffered saline (250 $\mu$l, 12.5 $\mu$g protein), pH 9.3, overnight at room temperature and the surface was saturated with 0.5 percent of BSA in 0.05 M Tris-HCl buffered saline, pH 7.7, containing 0.05 percent of NaN$_3$, for one hour at room temperature. The plasma specimen (200 $\mu$l) was incubated for two hours at 40° C. in a coated tube. After three washings with saline solution the second incubation with labelled antibody (10 ng/tube) was performed for one hour at 40° C. in 200 $\mu$l of 0.05 M Tris-HCl buffered saline, pH 7.7, containing 0.05 percent of NaN$_3$ and 5 percent of both normal human and sheep serum. The tubes were washed three times with saline solution and the europium ion was released and measured as described in experiment 1.

Figure 3:
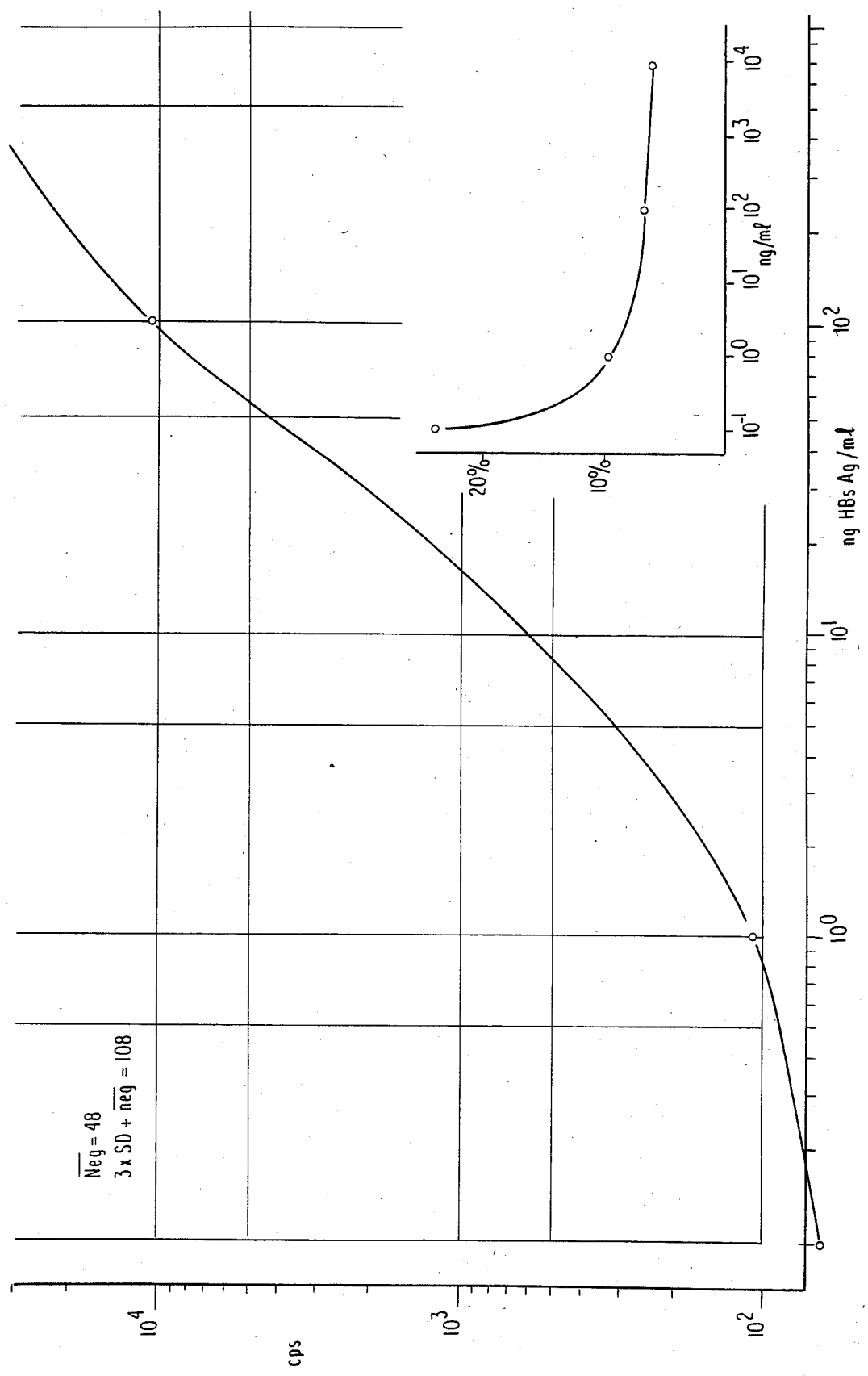
FIG. 3 is a graph of the assay data from different amounts of HBsAg in Example 2.

The result of the assay using different amounts of HBsAg is shown in FIG. 3.

What is claimed is:

1. In a method for fluorescence spectroscopic determination of a biological substance provided with a marker consisting of a lanthanide chelate complex formed of a lanthanide coupled to the substance via a chelate forming compound, by excitation by a short radiation pulse, and detection of the fluorescence of the marker when the fluorescence from any noise source has substantially ceased, wherein the improvement comprises, adding, before the determination, a solution that brings the pH to 3.5 or below and contains a detergent and a $\beta$-diketone to dissociate the lanthanide ion from the chelate complex and to transfer the dissociated lanthanide ion into a fluorescent form to enable the determination in the solution.

2. Method according to claim 1 wherein the solution is an aqueous solution.

3. Method according to claim 1 wherein the lanthanide is europium.

4. Method according to claim 1 wherein the detergent is an alkyl aryl polyether alcohol.

5. Method according to claim 1 wherein the β-diketone is 2-naphthoyltrifluoroacetone or 1-naphthoyltrifluoroacetone.

6. Method according to claim 1 wherein the β-diketone is 2-naphthoyltrifluoroacetone, 1-naphthoyltrifluoroacetone, p-methoxybenzoyltrifluoroacetone, p-fluoribenzoyltrifluoroacetone, benzoyltrifluoroacetone, furoyltrifluoroacetone, naphthoylfuroylmethane, dithenoylmethane and dibenzoylmethane.

7. Method according to claim 1 wherein the solution contains a Lewis base.

8. Method according to claim 3 wherein the Lewis base is trioctylphosphineoxide.

9. Method according to claim 1 wherein the chelate forming compound is an EDTA-analogue.

10. Method according to claim 1 wherein the solution is a buffer, having a pH of 2.8 to 35, which includes 10 to 100 μM of 2-naphthoyltrifluroacetone, 10 to 100 μm of trioctylphosphineoxide and 0.1 to 0.5 percent of an alkyl aryl polyether alcohol.

* * * * *